United States Patent [19]

Olson et al.

[11] Patent Number: 5,122,129
[45] Date of Patent: Jun. 16, 1992

[54] SAMPLER COUPLER DEVICE USEFUL IN THE MEDICAL ARTS

[76] Inventors: Donald J. Olson, 605 Briarwood La., San Dimas, Calif. 91773; Judith A. McGrail, 25560 River Bend Dr. #D, Yorba Linda, Calif. 92686

[21] Appl. No.: 521,186

[22] Filed: May 9, 1990

[51] Int. Cl.⁵ ............................................. A61M 25/00
[52] U.S. Cl. .................................. 604/905; 604/411; 604/240; 604/243; 604/283
[58] Field of Search ............... 604/407, 411, 414, 415, 604/240, 243, 905, 283

[56] References Cited

U.S. PATENT DOCUMENTS

| Re. 29,656 | 6/1978 | Chittenden et al. | 604/411 |
|---|---|---|---|
| 1,737,844 | 12/1929 | Heineman | |
| 1,842,134 | 1/1932 | Waite | |
| 2,689,562 | 9/1954 | Adams | |
| 3,788,369 | 1/1974 | Killinger | 141/330 |
| 3,882,909 | 5/1975 | Ogle | 604/411 |
| 3,976,073 | 8/1976 | Quick et al. | 604/405 |
| 4,161,949 | 7/1979 | Thanawalla | 604/411 |
| 4,445,896 | 5/1984 | Gianturco | 604/238 |
| 4,505,709 | 3/1985 | Froning et al. | 604/411 |
| 4,543,101 | 9/1985 | Crouch | 604/411 |
| 4,601,703 | 7/1986 | Herlitze | 604/86 |
| 4,607,671 | 8/1986 | Aalto | 141/329 |
| 4,636,204 | 1/1987 | Christopherson | 604/283 |
| 4,675,020 | 6/1987 | McPhee | 604/411 |
| 4,676,775 | 6/1987 | Zolnierczyk | 604/28 |
| 4,759,756 | 7/1988 | Forman | 604/413 |
| 4,787,429 | 11/1988 | Valentini | 141/383 |
| 4,943,283 | 7/1990 | Hogan | 604/405 X |
| 4,959,053 | 9/1990 | Jang | 604/411 X |
| 4,998,925 | 3/1991 | Al-Sioufi et al. | 604/905 X |

*Primary Examiner*—Robert A. Hafer
*Assistant Examiner*—Kerry Owens

[57] ABSTRACT

The sample coupler device is used to connect a sample collector container to a pipe used to transport gases or liquids. The coupler device permits collecting of blood or intravenous fluid sample material without it becoming contaminated. The coupler's most significant feature is the combination of the conical snout on the housing containing the integral feeder tube so that the blood or intravenous fluid may be collected without utilizing any external needles. This is significant when the person to whom this intravenous feeding system is connected has been exposed to Acquired Immune Deficiency Syndrome, hepatitis or any other non-curable or potentially fatal malady.

3 Claims, 4 Drawing Sheets

SAMPLER COUPLER DEVICE USEFUL IN THE MEDICAL ARTS

FIELD OF THE INVENTION

The sampler coupler device relates to collecting samples of fluidic substances from an artery or transport piping without utilizing an injection needle, while still preserving the integrity of the sample collected. Consequently, the inherent danger of contamination or secondary infection through, e.g., non-purposeful human contact with a tainted needle is eliminated.

DESCRIPTION OF THE PRIOR ART

A patentability search was conducted in the United States Patent Office on Mar. 28, 1990. That search was directed to a contained blood withdrawal system. The search included examination of the patents listed herein below, from Class 128, subclass 271 and 272; and Class 604, subclass 240, 411 through 415.

|  | U.S. Pat. No. | Inventor |
| --- | --- | --- |
| Class 128: | 1,842,134 | Waite |
|  | 2,689,562 | Adams, et al. |
|  | 4,445,896 | Gianturco |
|  | 4,601,703 | Herlitze |
|  | 4,759,756 | Forman, et al. |
|  | 4,787,429 | Valentine, et al. |
| Class 604: | 1,737,844 | Heineman |
|  | 4,607,671 | Aalto, et al. |
|  | 4,636,204 | Christopherson |
|  | 4,675,020 | McPhee |
|  | 4,676,775 | Zolnierczyk |

No patents were discovered which disclose a blood withdrawal system which offers protection from inadvertant contamination to the sample, and inadvertant secondary infection to the handlers. The art considered pertinent will be discussed herein before proceeding to the other cited patents.

The patent to Forman U.S. Pat. No. 4,759,756 discloses a bag adapter having needle ribs (224) and wall portions (226). Unlike the subject blood collector, the Forman device is used for reconstituting drugs, and offers no provision for protecting the operator from inadvertent contamination by contact between the operator and the exposed and contaminated portions of the Forman device.

The patent to Gianturco U.S. Pat. No. 4,445,896 discloses a connector (11), tubular coupler (22a), and a passage (21). Although the Gianturco device does permit repeated access to the contents of a catheter, it requires the use of an injection needle, which is considered very undesirable for reasons stated herein below.

The patent to Adams, et al., U.S. Pat. No. 2,689,562 discloses a device to collect blood from a donor, utilizing an injection type needle whose hazards are disclosed herein below.

The balance of the patents disclosed in this first group are not relevant to the invention at issue, but instead address either mixing of different drugs or injecting devices for same.

The patent to Aalto, et al., U.S. Pat. No. 4,607,671 discloses a device (10) in their FIGS. 2 and 3, having a sheath (70) installed on a vial (12) by pushing needle end (50) through stopper (20). The Aalto device is a drug reconstituting device, with no provisions to avoid contaminating the operator with the drug.

The patent to McPhee U.S. Pat. No. 4,675,020 discloses a connector for attaching a flow line to a vial. [See: McPhee FIGS. 1, 2, and 5.] This device has no provisions to avoid contaminating the operator with the drug it is delivering. This device also utilizes an exposed injection needle which is considered undesirable for the reasons stated herein below.

The balance of the patents in this group disclose connectors, but are only of general interest. None of the patents disclosed the combination of features of the sampler coupler device and consequently they could not be substituted for it to collect blood which is free from possible contamination to the blood sample or to the handler.

BACKGROUND OF THE INVENTION—DESCRIPTION OF PRIOR ART

Often it becomes necessary to collect a sample of blood, fluid or gas from the closed circulatory systems of a human, animal or machine, and preserve this sample for further processing. The sample collected may be subjected to laboratory testing or evaluation, such that the integrity of the collected sample must be maintained during the collecting procedures. It is necessary to avoid secondary infection or contamination of the personnel collecting the sample, e.g. from the donor's intravenous medicament delivery system. For this reason, it is preferred that none of the apparatii being utilized to collect the sample have any exposed sharp points or edges which could inadvertently scratch or pierce the handler's skin, resulting in secondary infection or contamination to their own body's systems. This secondary infection becomes particularly worrisome when samples must be collected frequently; i.e., every few hours or when the donor or the one being medicated has a loathsome, incurable or fatal disease or when the medicament is a hazardous material. In those situations, where frequent samples must be collected, the probability of human error significantly rises.

The prior art for collecting blood samples from, e.g., the piping of an intravenous medicament delivery system of a patient being medicated or fed intravenously through an artery, requires the use of at least two sterile syringes, at least one injection needle mounted on one of the syringes and several collection vials. The known design components of intravenous medicament delivery systems include: a reservoir of medicament or the like, piping to transport the medicament, and an arterial entry needle. The transport piping assembly usually includes an integral four-way stopcock to access samples of blood or other material flowing through the delivery system piping. These stopcocks typically have an access port with a removable cap and a control lever to direct the through flow, side flow or non-flow of the fluid. The stopcock is therefore, a non-removable element of the delivery piping which connects the intravenous medicament reservoir to the arterial entry needle which is inserted into an artery on a patient or subject when in use.

Typically, the person who does the collecting of the samples, must gather together the above apparatii and some absorbent toweling or the like to absorb spillage. The stopcock directional lever is first moved from the through-flow position to the non-flow position. The cap is removed from the access port on the four-way stopcock and the end of the syringe to which an injection needle is customarily attached, is inserted into that access port. The known design of the syringe end effects a seal when it is forced home into the conical bore of the access port. The stopcock directional lever may then be moved to the side-flow position which permits fluid in the piping between the stopcock and the patient to empty from the piping through the stopcock into that first syringe. This flow is permitted to continue until the material being collected visually appears to be primarily fluid of the patient, as contrasted to intravenous medicament fluid. The stopcock is then returned to the non-flow position, and the first syringe is removed from the access port and replaced with the second syringe. The stopcock directional lever is again switched to the side-flow position and substantially pure patient fluid, blood or the like, is collected inside the second syringe, while it is forceably connected to the stopcock access port.

After the collecting of patient's fluid or material sample is complete, the stopcock directional lever is again placed in the non-flow position and the syringe is removed from the access port. The syringe is set aside while the stopcock directional lever is moved to its second side-flow position which permits intravenous medicament fluid to wash the patient fluid out through the access port. The wash through fluid is usually collected into some absorbent toweling which is then discarded. The stopcock directional lever is then returned to its non-flow position as the access port's cap is replaced over the port. Now the stopcock directional lever may be returned to its original through-flow position.

An injection needle is mounted onto each syringe containing the substantially pure patient fluid or blood so that the fluid may be injected through the self sealing capping membrane of evacuated container(s) of known construction. The evacuated container(s) are transported to the sample processing facility, while the syringes, needles, absorbent toweling and packing materials are all discarded in a proper infectious/hazardous waste container. It is critical to note that the acts involved in the manual handling of the sharp and now contaminated needles, and the now contaminated absorbent toweling present a grave danger of secondary infection or contamination, which could prove fatal to the personnel handling them, including physicians, nurses, laboratory staff and hospital staff.

SUMMARY OF THE INVENTION

The present invention solves, e.g., the problem of accidental infection or contamination by eliminating the exposure of medical or laboratory personnel to needles which, after they have become contaminated, may cut or puncture a handling person's skin, during use in collecting samples. The sampler coupler device allows for samples of blood, fluids or gases to be collected from a closed, arterial style feed-system, while also preventing contamination of the collected sample through exposure to an atmosphere outside of the closed system. The sampler coupler itself should be properly discarded after use.

The present invention is also directed to a sampler coupler device, which enables collecting of samples from a variety of closed systems of varying dimensions.

The sampler coupler device of the present invention includes a double-ended plastic sheath, which is removably mountable into the access port of a four-way stopcock. This stopcock is an integral element of an intravenous medicament delivery system. The sheath includes a substantially circular base and a skirt descending from the base. The skirt, of substantially cylindrical shape, includes a free-end opposite the base, and substantially parallel inner and outer surfaces. The cylindrical skirt and its free-end comprise the female end of the sheath. A flow path means is included in the sampler coupler device for placing the interiors of the sample-collection tube or vial and the stopcock in open communication. In a preferred embodiment, the evacuated container assembly entering means, the stopcock entering means, and the flow path means, comprise a single, hollow, single-pointed needle, i.e., a delivery tube, which is secured between its two ends within the base detail. This single pointed needle extends through the base. One portion of the needle is disposed substantially at the axis of the cylinder defined by the sheath. The pointed end is recessed from the free-end of the sheath skirt.

The portion of the needle which extends towards the free-end of the sheath in a preferred embodiment is enveloped within a rubber-like prolate drip boot. The boot's length is such that it extends substantially beyond the pointed end of the needle, when its opposite end extends to and is affixed to the base of the sheath. The boot serves to prevent atmospheric or other contamination to the pointed end of the needle, and to contain any fluid or gas drippage from the needle.

The other portion of the needle extends past the opposite side of the base, and in a preferred embodiment is encased in a continuous and substantially solid conical feature, the outer surface being of known construction. This outer surface of the conical feature, is sealably mountable to an access port of a stopcock, also of known construction, enabling an interference fit between the stopcock and the sampler coupler device. The conical feature has a free-end, which is substantially flush with the non-pointed end of the needle. The conical feature includes a lock-in-place feature. The conical feature with the integral hollow needle and the lock-in-place feature comprise the male end of the double-ended sheath. The lock-in-place feature is substantially cylindrical about the axis of the needle. One end of the lock-in-place feature is affixed to a base end of the conical feature. The free-end of this lock-in-place feature extends substantially to the free-end of the conical feature. The lock-in-place feature's cylindrical periphery may be striated or otherwise roughened to ease gripping it. The lock-in-place feature's inside surface is comprised of an internal screw-type thread of known construction. The lock-in-place feature is used to hold the sampler coupler's conical feature sealably mounted into the conical bore of the access port of the stopcock, thereby avoiding inadvertent disengagement. The free-end of the access port of the stopcock, includes an external thread of known construction, which mates to the thread within the cylinder of the lock-in-place feature.

Further objects and advantages of the invention will become apparent from a consideration of the drawings and ensuing detailed description of it.

DESCRIPTION OF DRAWING FIGURES

FIG. 1 SAMPLER COUPLER DEVICE IN MEDICAL APPLICATION: Shown is an exploded perspective view of a preferred embodiment of the invention, illustrating the attachment of the sampler coupler device to a four-way stopcock on an intravenous medicament delivery system connected to a human.

FIG. 2 SAMPLER COUPLER DEVICE; ASSEMBLY: Shown is a plan view of the sampler coupler device.

FIG. 3 SAMPLER COUPLER DEVICE; END VIEW: Shown is an end view of the female end of the sampler coupler device.

FIG. 4 SAMPLER COUPLER DEVICE; SECTIONAL VIEW: Shown is a sectional view of the sampler coupler device.

FIG. 5 EVACUATED CONTAINER; ASSEMBLY: Shown is a plan view of a typical sample collector vial, which is an evacuated container with a rubber-type stopper in place.

FIG. 6 SAMPLER COUPLER DEVICE WITH EVACUATED CONTAINER; SECTIONAL VIEW: Shown is a sectional view of the sampler coupler device with an evacuated container style sample collector vial in place.

FIG. 7 STOPCOCK; ASSEMBLY: Shown is a plan view of a typical four-way stopcock of known construction.

FIG. 8 SAMPLER COUPLER KIT: Shown is a perspective view of a kit including: A sampler coupler, two disposable collector vials (evacuated container style), and an access port cap, in a sterile see-through "peel" type wrapping, of known construction.

REFERENCE NUMERALS IN DRAWINGS

| Reference Number | Reference Name |
| --- | --- |
| 10 | Sampler Coupler Device (Assembly) |
| 11 | Lock-in-Place Feature |
| 12 | Conical Feature |
| 13 | Integral Internal Opening |
| 14 | Male End |
| 15 | Base |
| 16 | Double Ended Sheath |
| 17 | Female End |
| 18 | Skirt |
| 19 | Internal Thread (Luer Lock) |
| 20 | Delivery Tube, Double Ended |
| 21 | Pointed End of Delivery Tube |
| 22 | Drip Boot |
| 23 | Evacuated Container (Assembly) |
| 24 | Sealing Membrane/Stopper |
| 25 | Evacuated Chamber |
| 26 | Four-Way Stopcock (Assembly) |
| 27 | Directional Lever |
| 28 | Access Port |
| 29 | Conical Bore |
| 30 | Threaded Lip (Luer Lock) |
| 31 | Reservoir Pipe Port |
| 32 | Arterial Pipe Port |
| 33 | Intravenous Medicament Delivery System (Assembly) |
| 34 | Medicament |
| 35 | Medicament Reservoir |
| 36 | Reservoir Transport Pipe |
| 37 | Arterial Transport Pipe |
| 38 | Artery Entry Needle |
| 39 | Cap (Luer Lock) |
| 40 | Sample Material |

DETAILED DESCRIPTION OF A PREFERRED EMBODIMENT

A preferred embodiment of the sampler coupler device of the present invention illustrated in FIGS. 1 through 8, inclusive.

Figure 1:
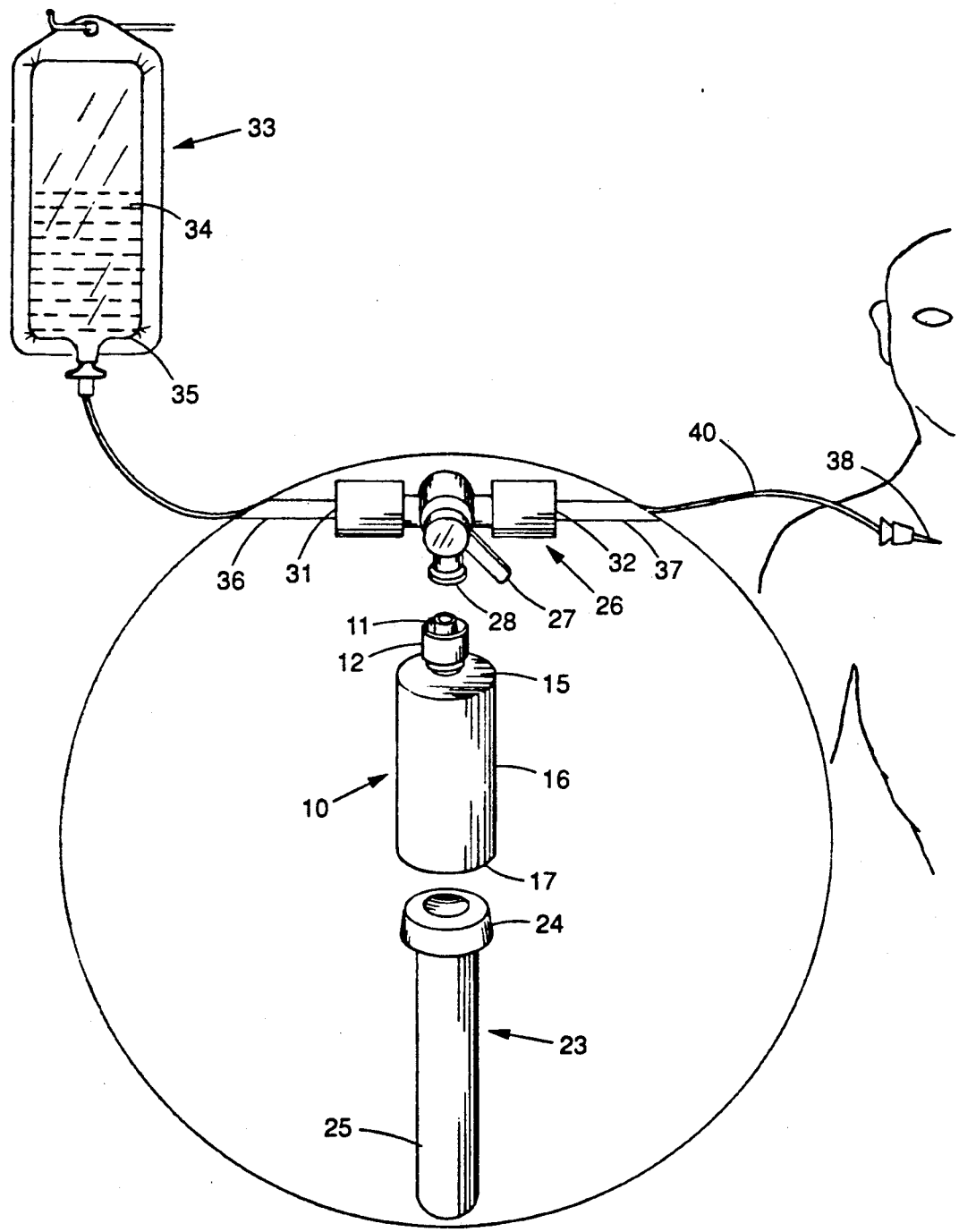

FIG. 1 illustrates a sampler coupler device 10 to be coupled to the 4-way stopcock 26, with a rigid evacuated container 23 mounted within the free-end 17 of the sampler coupler sheath 16.

The four-way stopcock 26 may be of standard construction as used throughout the medical industry, such as a Burron Discofix (by Burron Medical Inc.). The four-way stopcock 26 is typically made of optically transparent rigid plastic, and includes a directional lever 27 for controlling which port 28 or 31 and 32 of the four-way stopcock, the gas or liquid material may enter or exit through. An access port 28 on the four-way stopcock 26 is utilized to couple the sampler coupler 10 to the four-way stopcock 26. The four-way stopcock 26 has one end of transport pipe 36 attached to its reservoir pipe port 31, with the opposite end of transport pipe 36 attached to the medicament reservoir 35. The four-way stopcock 26 has one end of arterial transport pipe 37 attached to its arterial pipe port 32, with the opposite end of arterial transport pipe 37 attached to the artery entry needle 38. With the directional lever 27 in the through-flow position, the flow path means are included within the four-way stopcock 26 for placing the interiors of reservoir 26 and entry needle 28 in open communication.

Figure 7:
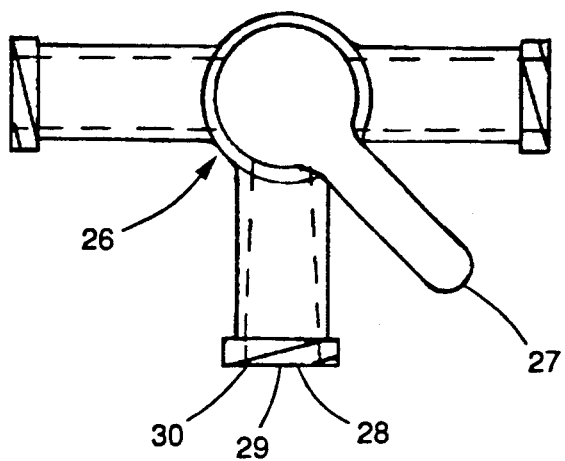

The access port 28 as shown in FIG. 7, includes a threaded external raised lip 30, surrounding the periphery of the free-end, of known construction typically identified as a Luer Lock construction. The access port 28 is selectively in communication with pipe 36, pipe 37, or blocked from all communication as controlled by the user selected position of directional lever 27. Initially, the directional lever 27 is placed in the non-flow or blocked position, and the cap (if any), is removed from access port 28.

Figures 2, 4:
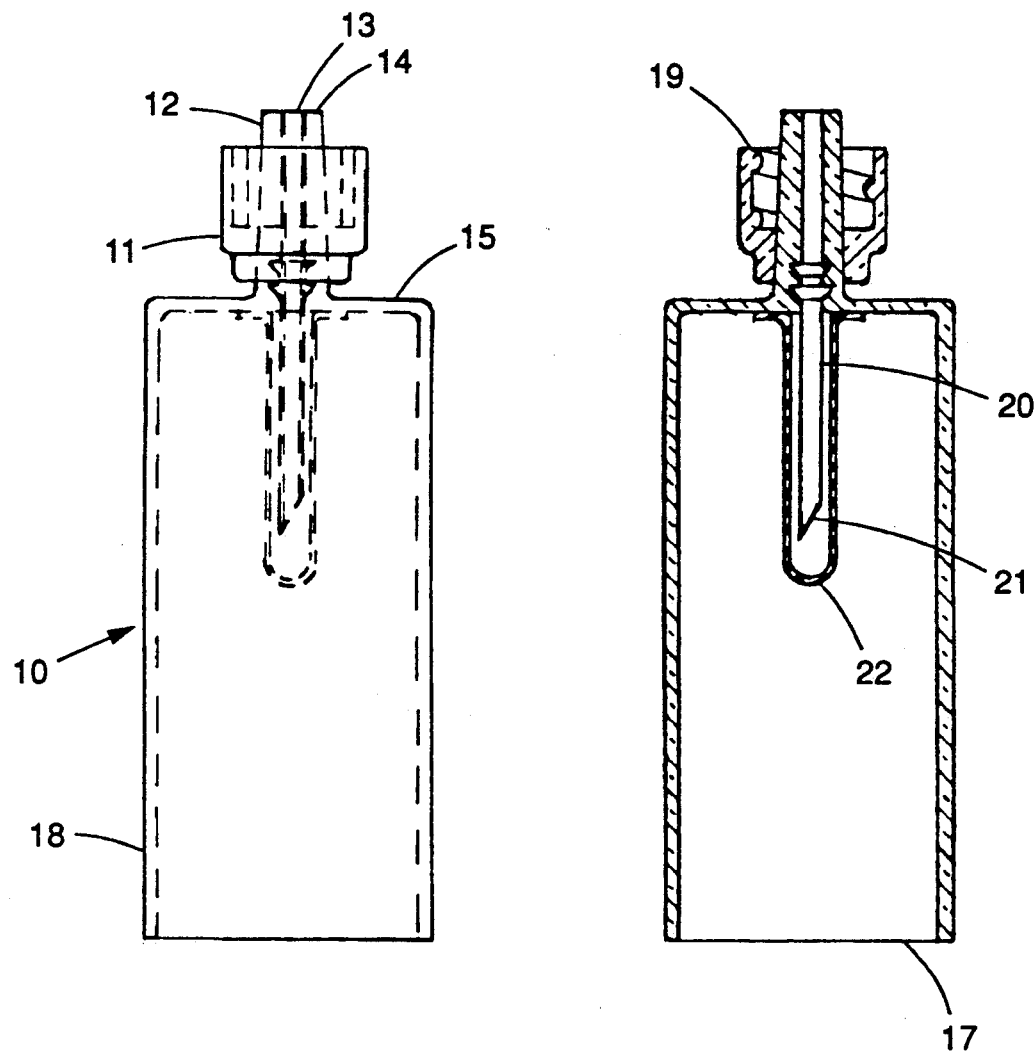
Figure 3:
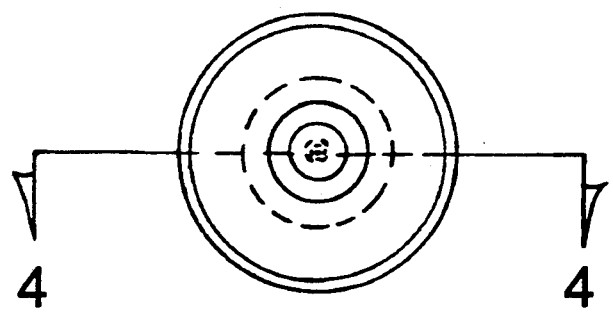

In FIG. 2, the free-end 14 of the conical feature 12 of the sampler coupler 10 is inserted into the access port 28 of the four-way stopcock 26, while the sampler coupler is rotated radially about its axis. This causes the internal thread 19, as shown in FIG. 4, of the lock-in-place feature 11 to engage the threaded lip 30, as shown in FIG. 7, until the conical feature 12, as shown in FIG. 2, bottoms tightly into the conical bore 29, as shown in FIG. 7, effecting a seal.

Figure 5:
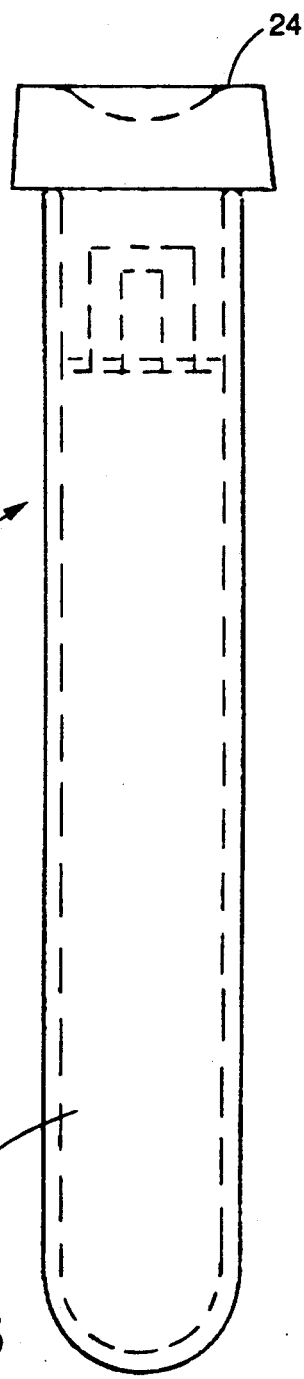
Figure 8:
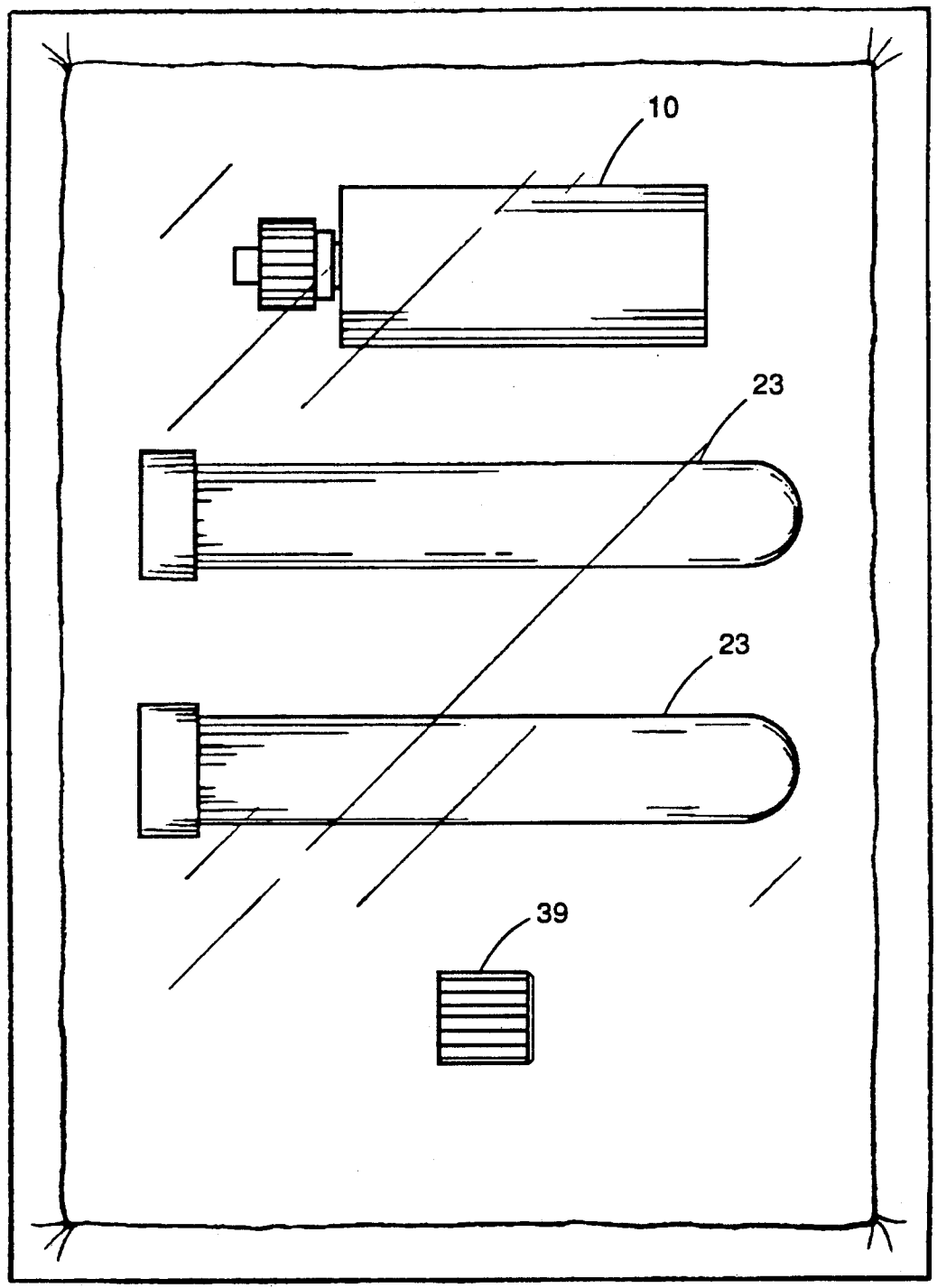

While the sampler coupler 10 is in this sealed and locked-in-place position, the various evacuated containers 23, as shown in FIG. 5, are inserted and filled with the blood or target fluid 40, then withdrawn completely from the sampler coupler 10. In a preferred embodiment, the evacuated containers(s) 23, which are disposable, may be constructed of optically transparent rigid plastic, and included in a kit form with the sampler coupler, as shown in FIG. 8. In a preferred embodiment, evacuated container 23, may be of glass construction such as a Vacutainer (manufactured by Becton Dickinson Inc.). In a preferred embodiment, the sample coupler 10 is of an optically transparent or translucent material.

Figure 6:
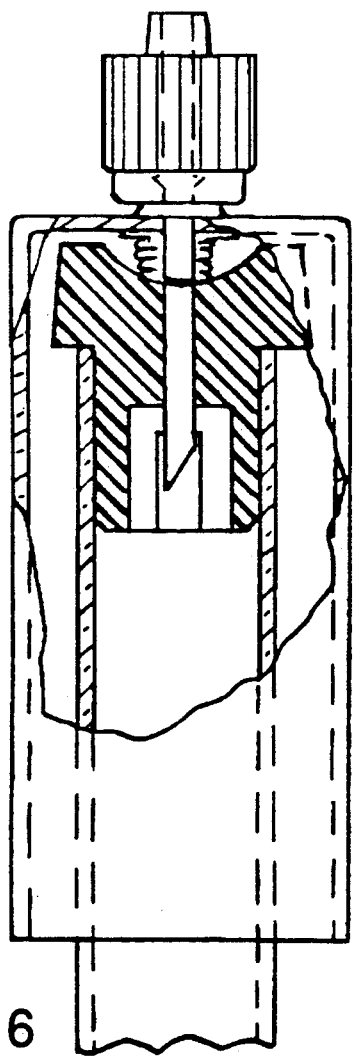

The stopper 24 in the end of the first evacuated container 23 is inserted through the free end 17 of the sheath 16, as shown in FIG. 1, until the stopper 24, as shown in FIG. 5, rests near the surface of the base 15, as shown in FIG. 2, of the sheath. In a preferred embodiment, the stopper 24 should be of a rubber-like material. In a preferred embodiment, the sheath 16 is of sufficient length to protect the evacuated container 23 from inadvertent disengagement, but will still permit sufficient amount of the evacuated container 23 to extend outside sheath 16 so that it may be easily gripped by the fingers and removed, as shown in FIGS. 4 and 5. The action of the stopper 24 against the drip boot 22 causes it to be pierced through by the pointed end 21 of the delivery tube 20. Thus, the conical bore 29 of the four-way stopcock is placed in open communication with the integral internal opening 13 of the delivery tube 20, which is in open communication with the evacuated chamber 25 of the evacuated container 23. In a preferred embodiment, the delivery tube 20 is constructed of metal or similarly rigid material, and is of sufficient length to penetrate completely through the stopper 24, as shown in FIGS. 5 and 6. The directional lever 27 may now be moved to the position which permits communication between the transport pipe 37 and the evacuated chamber 25 for the period of time that is necessary for the medicament 34 to be washed out through pipe 37 by the blood or fluid 40, which will become the collection target, as shown in FIG. 1. The directional lever 27 is returned to the non-flow position, while the first evacuated container 23 is completely removed from the sampler coupler 10, as shown in FIG. 1, and discarded. The evacuated container(s) 23 will be utilized to collect and hold the blood sample(s) for processing. Successive evacuated containers 23 may then be inserted and filled. As each evacuated container 23 is withdrawn off delivery tube 20, the drip boot 22 re-envelopes the delivery tube 20 to contain any drippage.

After completion of the collection of the target fluid or blood 40, a final evacuated container 23 is inserted as shown above into the sampler coupler 10. The directional lever 27 is then moved to permit the reservoir transport pipe 36 to be in open communication with the access port 28 to permit the medicament 34 to wash the target fluid 40 out of the access port 28. The directional lever 27 is again returned to the non-flow position and the sampler coupler 10 is then completely uncoupled from the 4-way stopcock 26, and discarded. The new sterile cap 39, as shown in FIG. 8, is installed over access port 28. Directional lever 27 is then returned to its original through-flow position where reservoir transport pipe 36 is again in open communication with arterial transport pipe 37. The original cap which was in place on stopcock 12, is presumed contaminated and is discarded.

We claim:

1. A coupler device for coupling a sample collection container to a distribution system for gasses or liquids, said device comprising:
    a body having a first end and a second end, the second end including a rigid delivery tube, and a rubber-like boot, the boot being of sufficient dimension to contain the contents of the delivery tube, while enveloping said tube;
    a means for coupling the first end of said body to the distribution system;
    a longitudinal axis;
    an integral internal opening as an axial passageway which allows open communication through the device; and
    a means for delivering sample material into a collection container from within the second end.

2. A device for coupling a sample collector vial to a distribution mechanism on a transport pipe, said device comprising:
    a body having a first end and a second end, a longitudinal axis, and an integral internal opening extending from the first end of said body to the second end of said body, said first end of said body of such construction to sealably mate to a distribution mechanism, such that its integral internal opening is in open communication with the interior of said distribution mechanism, said body comprising a first substantially cylindrical wall at said second end of said body that is concentric to said longitudinal axis; and
    a first blind recess lock-in-place feature affixed concentrically, on said first end of said body to permit fixed attachment of said body to the distribution mechanism, such that their integral internal openings remain in open communication;
    the second end of the body comprising a first substantially cylindrical wall, a first blind recess within said first cylindrical wall, concentric to said longitudinal axis and open to said second end of the body, and a hollow delivery tube, the integral internal opening of which defines the longitudinal axis of the device, and which extends substantially into the blind recess, the hollow delivery tube being enveloped in a permanently attached rubber-like boot for preventing contamination to said delivery tube, and the boot being sufficiently larger than the delivery tube to contain any drippage from the tube inside the boot, to prevent inadvertent contamination to handling personnel by the drippage from the tube.

3. A device for coupling a sample collector vial to a distribution mechanism on a transport pipe, said device comprising:
    a body having a first end and a second end, a longitudinal axis, and an integral internal opening extending from the first end of said body to the second end of said body, said first end of said body of such construction to sealably mate to a distribution mechanism, such that its integral internal opening is in open communication with the interior of said distribution mechanism, said body comprising a first substantially cylindrical wall at said second end of said body that is concentric to said longitudinal axis; and
    a first blind recess lock-in-place feature affixed concentrically, on said first end of said body to permit fixedly attaching said body, to the distribution mechanism, such that their integral internal openings remain in open communication;
    the second end of the body comprising a first substantially cylindrical wall, a first blind recess within said first cylindrical wall, concentric to said longitudinal axis and open to said second end of the body, and a hollow delivery tube, the integral internal opening of which defines the longitudinal axis of the device, and which extends substantially into the blind recess, the hollow delivery tube being enveloped in a rubber-like boot, which prevents contamination to the delivery tube, and contains any drippage from the delivery tube inside the boot, to help prevent inadvertent contamination to handling personnel by the drippage from the delivery tube;
    the first end of the body having a conical cylinder of substantially similar dimensions of a standard injection syringe end used to administer medicaments.

* * * * *